United States Patent
Fan et al.

(10) Patent No.: US 12,175,565 B2
(45) Date of Patent: Dec. 24, 2024

(54) METHODS AND SYSTEMS FOR CONTRAST-TO-NOISE EVALUATION OF COMPUTED TOMOGRAPHY SYSTEMS

(71) Applicant: GE Precision Healthcare LLC, Wauwatosa, WI (US)

(72) Inventors: Jiahua Fan, Waukesha, WI (US); Jonathan S. Maltz, Oakland, CA (US); Norbert Joseph Pelc, Aptos, CA (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 358 days.

(21) Appl. No.: 17/657,313

(22) Filed: Mar. 30, 2022

(65) Prior Publication Data
US 2023/0309935 A1     Oct. 5, 2023

(51) Int. Cl.
*A61B 6/03*     (2006.01)
*A61B 6/00*     (2006.01)
*G06T 11/00*     (2006.01)
*G06V 10/30*     (2022.01)

(52) U.S. Cl.
CPC .............. *G06T 11/008* (2013.01); *A61B 6/03* (2013.01); *A61B 6/032* (2013.01); *A61B 6/4429* (2013.01); *G06T 11/006* (2013.01); *G06V 10/30* (2022.01)

(58) Field of Classification Search
CPC ....... A61B 6/032; A61B 6/4429; A61B 6/583; A61B 6/58; A61B 6/03; G06V 10/30; G06T 11/006; G06T 11/008
See application file for complete search history.

(56) References Cited

U.S. PATENT DOCUMENTS

| | | | |
|---|---|---|---|
| 2003/0048867 A1* | 3/2003 | Acharya | A61B 6/583 378/18 |
| 2011/0293161 A1* | 12/2011 | Yi | A61B 6/4233 382/131 |
| 2015/0238160 A1* | 8/2015 | Flohr | A61B 6/482 378/8 |
| 2019/0167218 A1* | 6/2019 | Hsieh | A61B 6/5241 |

* cited by examiner

*Primary Examiner* — David P Porta
*Assistant Examiner* — Fani Polyzos Boosalis
(74) *Attorney, Agent, or Firm* — McCoy Russell LLP

(57) ABSTRACT

Methods and systems are provided for contrast-to-noise evaluation in medical imaging systems. In one embodiment, a method includes positioning a phantom having a variable width cross-section within a gantry of a computed tomography (CT) system so that the variable width cross-section is perpendicular to a central axis of the CT system, adjusting the phantom within the gantry of the CT system to a first imaging configuration having a first position and a first translation within the gantry, acquiring a first set of measurements from the phantom in the first imaging configuration, and calculating a contrast-to-noise ratio (CNR) of the CT system based on at least the first set of measurements and a first material density of an imaged slice of the phantom in the first imaging configuration.

18 Claims, 7 Drawing Sheets

METHODS AND SYSTEMS FOR CONTRAST-TO-NOISE EVALUATION OF COMPUTED TOMOGRAPHY SYSTEMS

FIELD

Embodiments of the subject matter disclosed herein relate to non-invasive diagnostic imaging systems, and more particularly, to computed tomography systems.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through a target volume, to acquire image data and to construct tomographic images (e.g., three-dimensional representations of the interior of the human body or of other imaged structures).

Different CT systems may produce different image qualities based on a type of hardware included in the system, a calibration of the system, or other settings. Therefore, metrics and practical approaches to determine image quality have been developed by vendors and imaging physicists. As imaging technology becomes increasingly advanced, it is also desirable to evaluate increases in image quality brought by newly developed hardware.

BRIEF DESCRIPTION

In one aspect, a method can include positioning a phantom having a variable width cross-section within a gantry of a computed tomography (CT) system so that the variable width cross-section is perpendicular to a central axis of the CT system, adjusting the phantom within the gantry of the CT system to a first imaging configuration having a first position and a first translation within the gantry, acquiring a first set of measurements from the phantom in the first imaging configuration, and calculating a contrast-to-noise ratio (CNR) of the CT system based on at least the first set of measurements and a first material density of an imaged slice of the phantom in the first imaging configuration.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Embodiments of the present disclosure will now be described, by way of example, with reference to the FIGS. 1-10, which relate to various embodiments for contrast-to-noise evaluation in medical imaging systems. Studying an image quality of computed tomography (CT) systems may be aided by selecting appropriate metrics for the evaluation and by using simplified practical approaches. As CT system technology becomes increasingly advanced, it is also desirable to evaluate image quality increases that newly developed hardware produces. One such metric for evaluating the image quality is the contrast-to-noise ratio (CNR), which is a ratio of contrast between signal in a given region compared to the background noise in the measurements. For example, the contrast may be due to a change in density or pathlength, and the noise may be produced due to random fluctuations in photon measurements in a detector array of the CT system (e.g., quantum noise) and may produce a grainy appearance in an otherwise homogenous region of the image. The CNR may be measured in tomographic images or, as in the present description, in projections. Increasing the CNR may help define structures of interest relative to background tissue, for example.

Current methods for evaluating the CNR may include the use of dedicated phantoms that are not used for other calibration or quality control procedures, which may increase a cost of operating the CT system as well as increase an amount of storage used. Further, the CNR assessment may include adding or removing phantom slabs during the imaging in order to change a pathlength through the phantom or a material density of the phantom. Such a process may be cumbersome and increase a duration of the evaluation.

Thus, according to embodiments disclosed herein, the CNR may be evaluated directly using data collected by the detector array using phantoms that may be routinely available for quality control, such as a water phantom or an acrylate plastic, glass, and silicone rubber phantom such as one specified by the American College of Radiology (ACR) for accreditation. The embodiments described herein may be used to evaluate the performance from energy-integrating detector (EID) CT systems as well as photon-counting CT (PCCT) systems. Notably, the CT system may be evaluated without adding or removing portions of the phantom, enabling faster and less cumbersome measurement. Further, because the data evaluated may be data collected by the detector array without additional data processing, such as image reconstruction, a computing power used during the evaluation may be reduced. In this way, the CNR may be more rapidly and easily obtained, enabling the CNR of both new and existing hardware to be more simply determined. As a result, the CT system may be more easily maintained, such as by identifying changes in the CNR over time, and upgraded, such as by replacing the detector array with one having a higher CNR.

Figure 1:
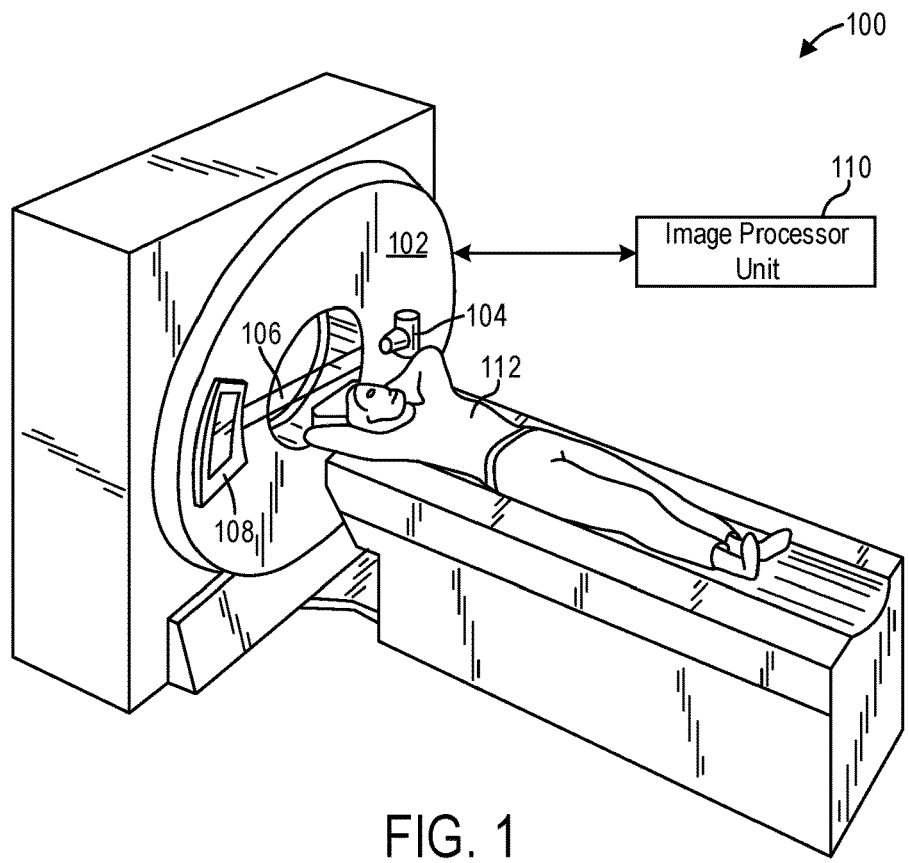
FIG. 1 shows a pictorial view of an imaging system, according to an embodiment.
Figure 2:
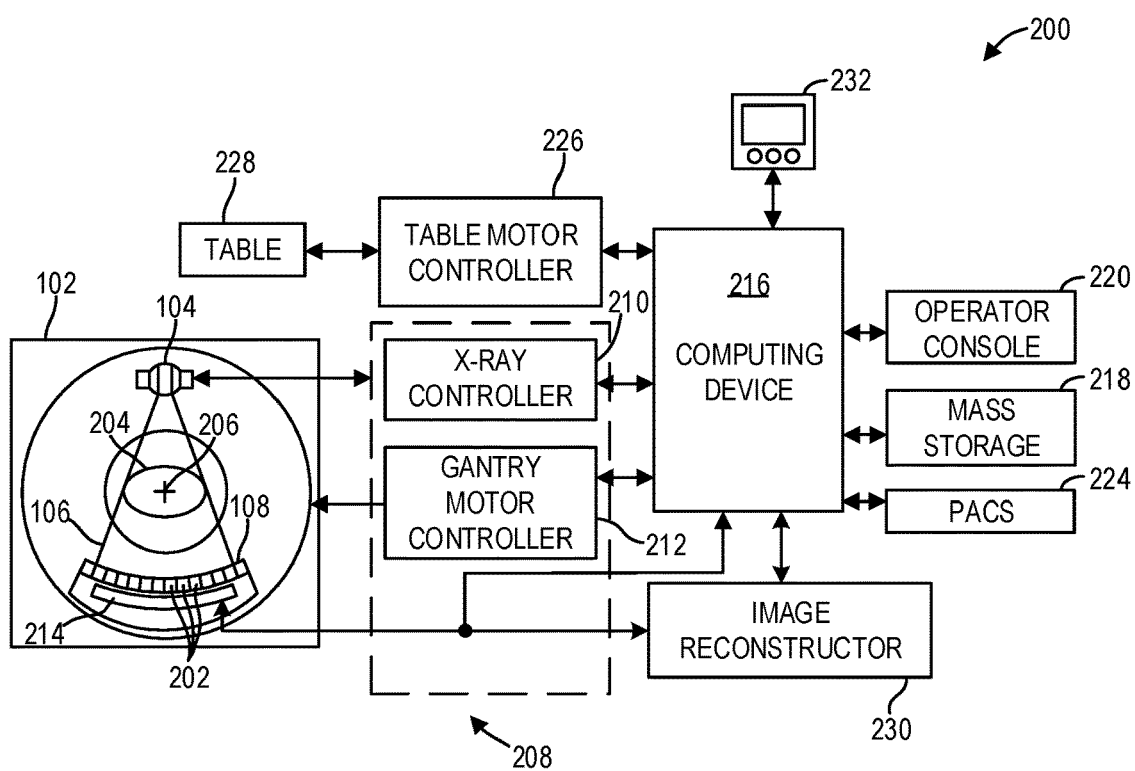
FIG. 2 shows a block schematic diagram of an exemplary imaging system, according to an embodiment.
Figure 3:
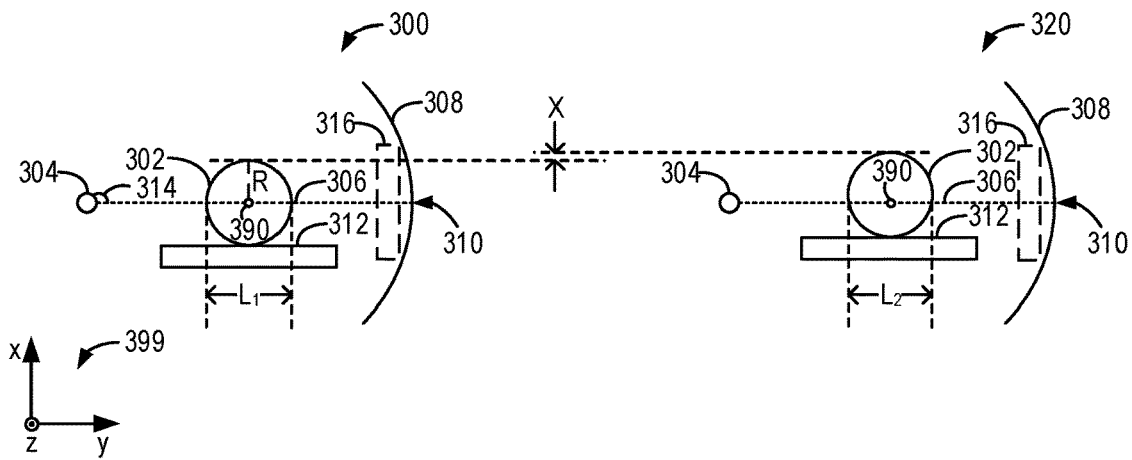
FIG. 3 shows a first example of using a phantom having a variable width cross-section to determine a contrast-to-noise ratio of an imaging system, according to an embodiment.
Figure 4:
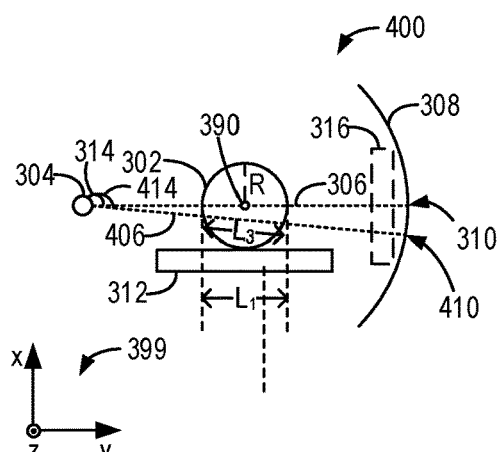
FIG. 4 shows a second example of using a phantom having a variable width cross-section to determine a contrast-to-noise ratio of an imaging system, according to an embodiment.
Figure 5:
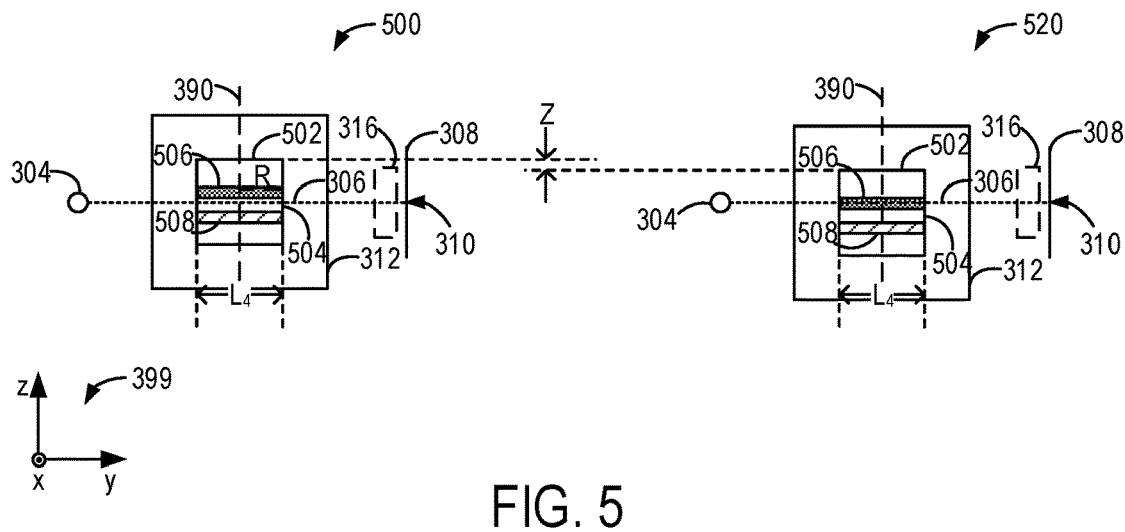
FIG. 5 shows a third example of using a phantom having different material density slices to determine a contrast-to-noise ratio of an imaging system, according to an embodiment.
Figure 6:
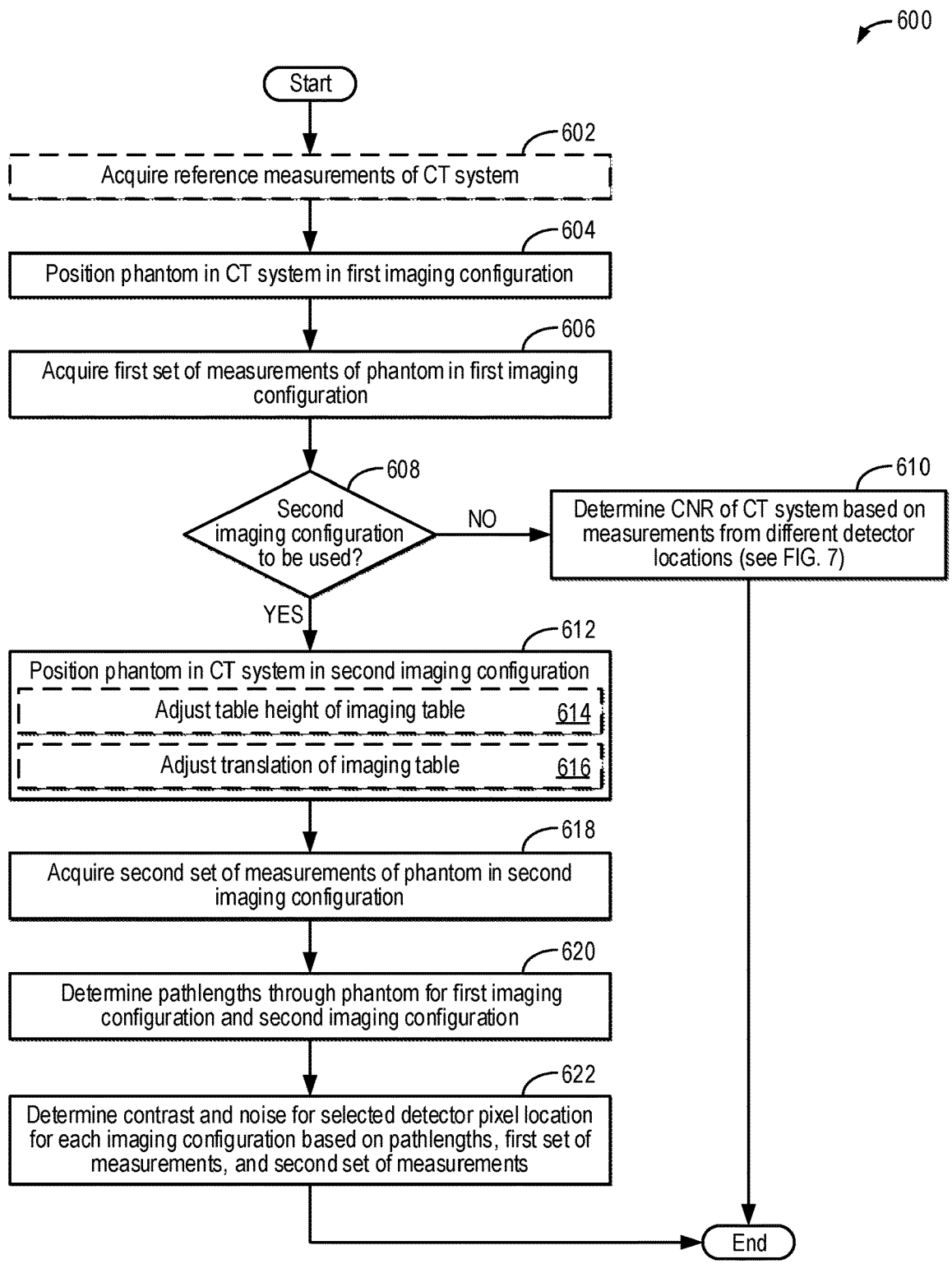
FIG. 6 is a flow chart illustrating a method for determining a contrast-to-noise ratio of an imaging system using different imaging configurations of a phantom within the imaging system, according to an embodiment.
Figure 7:
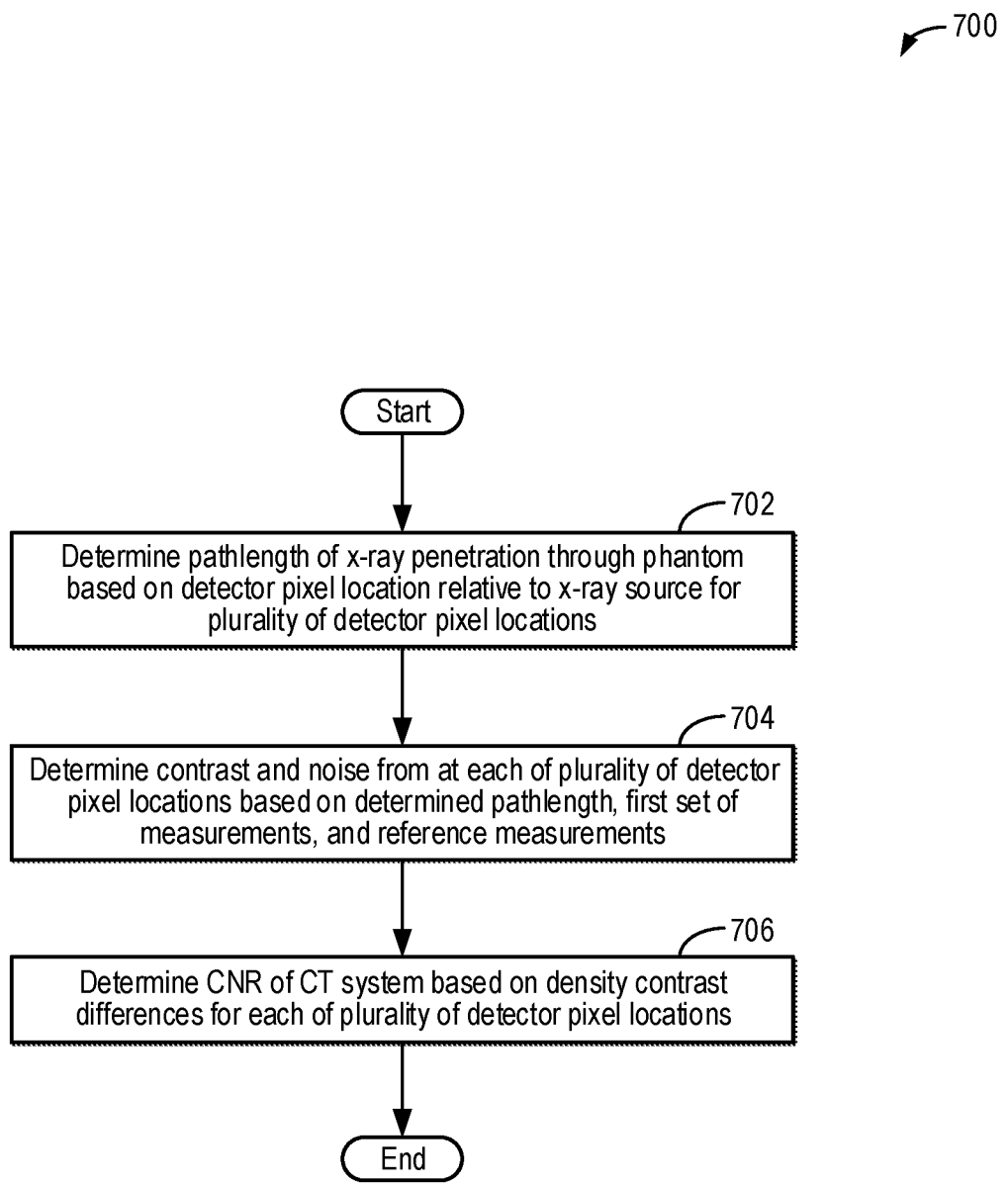
FIG. 7 is a flow chart illustrating a method for determining a contrast-to-noise ratio of an imaging system using a same imaging configuration of a phantom within the imaging system, according to an embodiment.
Figure 8:
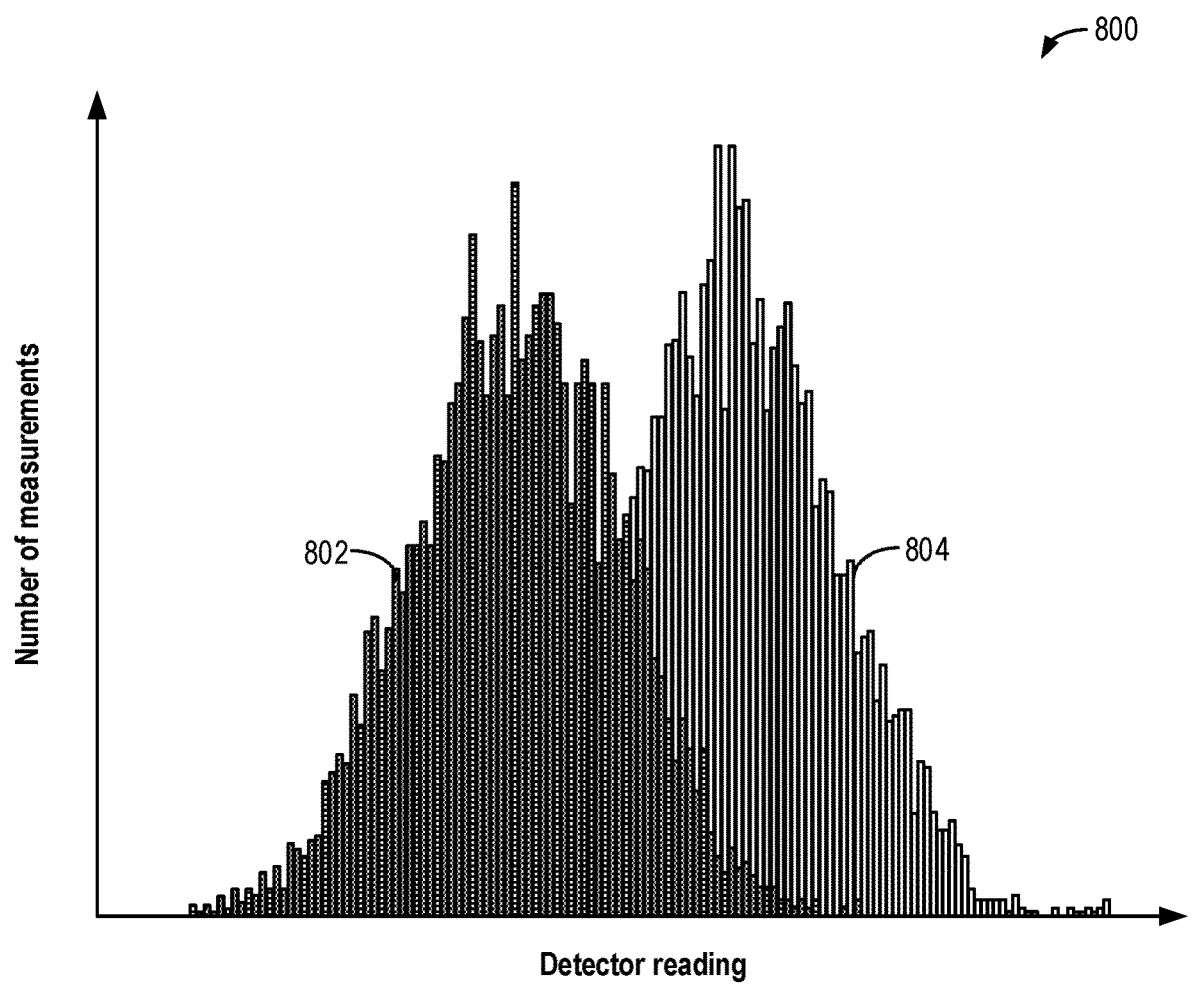
FIG. 8 shows exemplary measurements from a phantom compared with background measurements of an imaging system, according to an embodiment.
Figure 9:
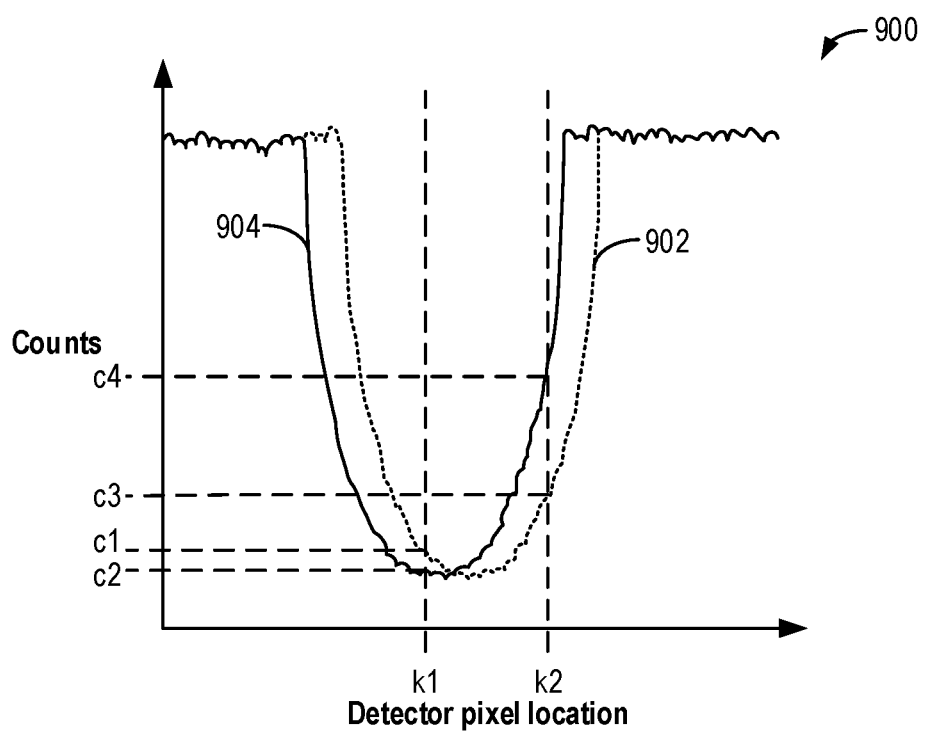
FIG. 9 shows an exemplary average signal output at a detector array when a phantom is in a first imaging configuration compared with a second imaging configuration, according to an embodiment of the disclosure.
Figure 10:
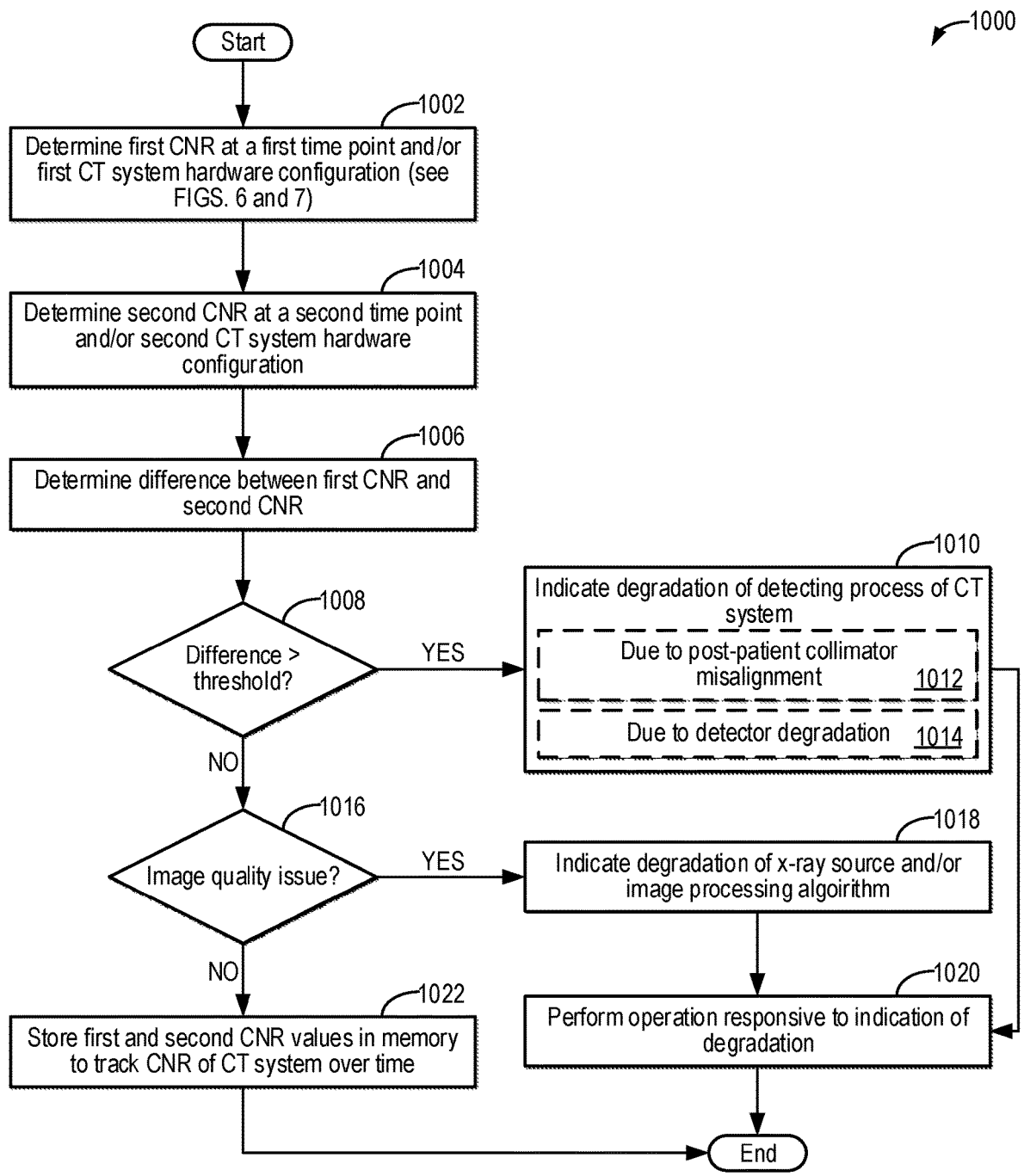
FIG. 10 is a flow chart illustrating a method for identifying degradation of the imaging system based on changes to the contrast-to-noise ratio, according to another embodiment of the disclosure.

An example of a CT imaging system that may be used to perform scans in accordance with the present techniques is provided in FIGS. 1 and 2. FIGS. 3-5 schematically illustrate different imaging configurations that may be used to acquire measurements for determining the CNR. For example, FIGS. 3 and 4 particularly highlight how a round water phantom may be used to determine the CNR, whereas FIG. 5 illustrates how a phantom having slices of differing material densities and compositions may be used. The CNR may be calculated based on changes in a detector output signal for different pathlengths through the phantom, such as according to the methods of FIGS. 6 and 7. For example, the pathlength may be changed for a same detector pixel location by adjusting a position of the phantom within the CT system, such as particularly described with respect to the method of FIG. 6. As another example, different pathlengths may be produced at different detector pixel locations for a same position of the phantom, such as elaborated with respect to FIG. 7. Notably, both methods enable the CNR to be determined without adding or removing additional phantom components within the CT system, enabling a faster acquisition process. Example measurements that may be obtained while executing the methods of FIGS. 6 and 7 are shown in FIGS. 8 and 9. Further, FIG. 10 provides a method that may be used to detect degradation of the CT system based on changes to the CNR over time.

Though a CT system is described by way of example, it should be understood that the present techniques may also be useful when applied to images acquired using other imaging modalities, such as tomosynthesis, C-arm angiography, radiography, fluoroscopy, hybrid modalities (e.g., a CT imaging system combined with a magnetic resonance imaging system), and so forth. For x-ray imaging systems, including CT, the contrast referred to in CNR may relate to phase contrast, small angle scattering, refractive index, and determinants of dark field imaging contrast. Phase contrast may be obtained with or without grating assemblies and with either monoenergetic or polyenergetic sources. The present discussion of a CT imaging modality is provided merely as an example of one suitable imaging modality.

FIG. 1 illustrates an exemplary CT system 100 configured for CT imaging. Particularly, the CT system 100 is configured to image a subject 112, such as a patient, an inanimate object such as a phantom, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring, for example, projection data at different energy levels corresponding to the patient. In some embodiments, the x-ray source 104 may enable dual-energy spectral imaging (such as GSI) by rapid peak kilovoltage (kVp) switching. In some embodiments, the x-ray detector employed is a photon-counting detector that is capable of differentiating x-ray photons of different energies. In other embodiments, the x-ray detector is an energy integrating detector in which the detected signal is proportional to the total energy deposited by all photons without specific information about each individual photon or its energy. In some embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. In some examples the image processor unit 110 may use an analytic image reconstruction approach such as FBP in addition to an iterative image reconstruction approach. In some embodiments, the image processor unit 110 may use a direct image reconstruction approach, such as using deep-learning trained neural networks.

In some CT imaging system configurations, the x-ray source 104 emits a cone-shaped beam which is collimated to lie within a plane of an X-Y-Z Cartesian coordinate system and generally referred to as an "imaging plane." The radiation beam passes through an object being imaged, such as the patient or subject 112. The beam, after being attenuated by the object, impinges upon the detector array 108 comprising radiation detectors. The intensity of the attenuated radiation beam received at the detector array 108 is dependent upon the attenuation of the radiation beam by the object. Each detector element of the array produces a separate electrical signal that is a measurement of the beam attenuation of a ray path between the source and the detector element. The attenuation measurements from all the detector elements are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, e.g., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, a positron emission tomography (PET), a single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple rotations or scans or two-dimensional arrays of detectors, a three-dimensional rendering of the object. One method for reconstructing an image from a set of projection data is referred to in the art as the filtered back projection technique. Transmission and emission tomography reconstruction techniques also include statistical iterative methods, such as maximum likelihood expectation maximization (MLEM) and ordered-subsets expectation-reconstruction techniques, as well as iterative reconstruction techniques. This process may convert the attenuation measurements from a scan into values called "CT numbers" or "Hounsfield units" (HU), which are used to control the brightness of a corresponding pixel on a display device.

To reduce the total scan time, a "helical" scan may be performed. To perform a "helical" scan, the patient is moved while the data for the prescribed number of slices are acquired. The position of the source with respect to the patient in such a system traces a helix. The helix mapped out by the source yields projection data from which images in each prescribed slice may be reconstructed.

As used herein, the phrase "reconstructing an image" is not intended to exclude embodiments of the present invention in which data representing an image are generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray beams 106 (see FIG. 1) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a central axis 206 for acquiring the projection data at the same or different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form at least one material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of one or more basis materials. The density image may be displayed to show these features. In traditional approaches to diagnosis of medical conditions, such as disease states, and more generally of medical events, a radiologist or physician may consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214. When coupled to an analog detector, the DAS 214 may be configured to sample analog data received from the detector elements 202 and convert the analog data to digital signals for subsequent processing. The DAS 214 may be further configured to selectively aggregate data from a subset of the detector elements 202 into so-called macro-detectors, as described further herein. The data collected and aggregated by the DAS 214 is transmitted to a computer or computing device 216. In one example, the computing device 216 stores the data in a storage device or mass storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which, in turn, may control a table 228 which may be a motorized table. Specifically, the table motor controller 226 may move the table 228 in one or more directions for appropriately positioning the subject 204 in the gantry 102 for acquiring projection data corresponding to the target volume of the subject 204. In one embodiment of the present application, the table motor controller 226 is used to position a phantom within the gantry via a table position.

As previously noted, the DAS 214 acquires the projection data provided by the detector elements 202. Subsequently, an image reconstructor 230 uses the x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200, and instead, the computing device 216 may perform one or more functions of the image reconstructor 230. Moreover, the image reconstructor 230 may be located locally or remotely and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes described further herein (such as the methods described below with reference to FIGS. 6, 7, and 10) may be stored as executable instructions in non-transitory memory on a computing device (or controller) in the imaging system 200. In an embodiment, the computing device 216 may include the instructions in non-transitory memory and may apply the methods described herein, at least in part, to determine a density contrast-to-noise ratio (CNR) of a scan of a phantom to evaluate the CNR of the imaging system 200. For example, high CNR may be beneficial during clinical scans that use density to differentiate between different tissues, such as white and gray matter differentiation in CT head imaging. In other embodiments, the image reconstructor 230 may include such executable instructions in non-transitory memory, and may apply the methods described herein to evaluate the CNR of the imaging system 200. In yet another embodiment, the methods and processes described herein may be distributed across the image reconstructor 230 and the computing device 216.

In one embodiment, the display device 232 allows the operator to evaluate the imaged anatomy or phantom, trigger aspects of the scans, and the like. The display device 232 may also allow the operator to select a region of interest (ROI) and/or request patient information, for example, via a graphical user interface (GUI) for a subsequent scan or processing.

As mentioned above, a phantom may be used to evaluate the CNR of a CT system, such as the CT system 100 of FIG. 1 and/or the imaging system 200 of FIG. 2. In general, different objects of known densities and differing pathlengths may be used to evaluate the CNR of the CT system. According to embodiments described herein, the CNR evaluation process may be simplified by using a single phantom that may already be employed for calibration and quality assurance tests. Thus, FIGS. 3-5 show exemplary embodiments of phantoms and CT system configurations for determining a CNR of the CT system are shown. As will be elaborated below, the CNR evaluation may use a uniform round phantom (e.g., FIGS. 3 and 4) or a non-uniform round phantom (e.g., FIG. 5) and determine a contrast between two imaging configurations to determine the CNR. Reference axes 399 are provided throughout FIGS. 3-5 in order to compare the relative arrangement of the components in the views. The x-direction of the reference axes 399 represents a vertical direction that is perpendicular (e.g., orthogonal) to a ground surface supporting the CT system and perpendicular to a central axis 390 of the CT system (e.g., the central axis 206 of FIG. 2). The y-direction of the reference axes 399 represents a horizontal direction that is parallel to the ground surface and perpendicular to the central axis 390 of the CT system. The central axis 390 may be centered within an opening of a gantry of the CT system, such as the gantry 102 shown in FIG. 1. The z-direction of the reference axes 399 represents a horizontal direction that is parallel to the ground surface and parallel to the central axis 390. As a further example, the z-direction comprises a patient axis along which a table motor controller (e.g., the table motor controller 226 of FIG. 2) may translate a table 312 in and out of the opening of the gantry.

The configurations shown in each of FIGS. 3-5 include an x-ray source 304 and a detector array 308. The x-ray source 304 may be the x-ray source 104 of FIG. 1, for example, and the detector array 308 may be the detector array 108 of FIG.

1, at least in some embodiments. The x-ray source 304 may be a focal spot or x-ray tube that produces x-ray radiation, for example. Although the same x-ray source 304 and detector array 308 are shown for each of FIGS. 3-5, it may be understood that different x-ray sources and detectors may be used without departing from the scope of this disclosure.

Primary x-rays are produced from the x-ray source 304, transmitted through an imaging subject (e.g., a phantom in the present examples), and detected by the detector array 308. In contrast, scattered radiation is secondary radiation produced by the deflection of x-rays by the imaging subject. Therefore, optionally, a pre-detector collimator 316 may be positioned between the imaging subject and the detector array 308 to reject x-rays that have a different incidence angle than the primary x-rays, thereby rejecting scattered radiation. The pre-detector collimator 316 may also be known as a post-patient collimator or an anti-scatter collimator or an anti-scatter grid. It may be understood that although not specifically shown, a pre-patient collimator that is positioned between the x-ray source 304 and the imaged object may also be included, at least in some embodiments.

Referring first to FIG. 3, a first imaging configuration 300 and a second imaging configuration 320 that may be used to determine the CNR by imaging a phantom 302 are shown. The phantom 302 has a variable width cross-section (e.g., in the x-y plane, as indicated by the reference axes 399). In the embodiment shown, the phantom 302 has a circular cross-section and a uniform composition. For example, the phantom 302 may be comprised of water-equivalent material (e.g., a 20 centimeter diameter or 30 centimeter diameter water phantom). The phantom 302 may be cylindrical, having a constant diameter (or radius) along a length (e.g., in the z-direction of reference axes 399) of the phantom 302 that is parallel to a length of the table 312. However, in other embodiments, the diameter of the phantom 302 may vary along its length. Additionally, in other embodiments, the variable width cross-section may have a different shape, such as a semi-circle or triangle, with a defined geometry. Further, a material density of the phantom 302 may be known (e.g., the density of water) and uniform throughout the phantom 302 such that any differences in contrast detected between first imaging configuration 300 and second imaging configuration 320 are not due to changes in the composition of the phantom 302 in an imaged slice.

In the first imaging configuration 300, the phantom 302 may be centered within the CT system and the x-ray source 304 may be centered on the phantom 302 such that an x-ray beam 306 emitted from the x-ray source 304 may pass through the diameter of the phantom 302 (e.g., where the phantom 302 is widest) and travel directly to a first detector pixel 310 of the detector array 308 (e.g., after passing through the pre-detector collimator 316, when included). For example, the x-ray beam 306 is parallel with the y-axis of reference axes 399 and may have a first angle 314 with the x-ray source 304. For example, the first angle 314 may be approximately 90 degrees. It may be understood that the x-ray source 304 may emit a plurality of x-ray beams in addition to the x-ray beam 306, such as a cone-shaped beam of x-rays, that are detected by other detector pixels of the detector array 308. The discussion of determining the CNR via the first imaging configuration 300 and the second imaging configuration 320 will be focused on the x-ray beam 306 and the first detector pixel 310, although it may be understood that similar calculations may be performed for different x-ray beams emitted from different angles with respect to the x-ray source 304 and detected at different detector pixels of the detector array 308 (such as will be described below with respect to FIG. 4). Further, it may be understood that the radius R and the first angle 314 are only shown in the first imaging configuration 300 for illustrative clarity but are also present in the second imaging configuration 320.

The x-ray beam 306 passes through the phantom 302 with a pathlength $L_1$ in the first imaging configuration 300. Because the phantom 302 and the x-ray source 304 are centered, the pathlength $L_1$ is equal to the diameter of the phantom 302 and is the largest pathlength through the phantom 302. The vertical positioning of the phantom 302 (e.g., in the x-direction of reference axes 399) is changed between the first imaging configuration 300 and the second imaging configuration 320 by adjusting a table height of the table 312 by a pre-determined amount. In the example shown, the table 312 is raised, resulting in a vertical displacement X between a first vertical position (e.g., first x-direction position) of the first imaging configuration 300 and a second vertical position of the second imaging configuration 320.

The vertical adjustment of the table 312 results in a pathlength $L_2$ of the penetration of the x-ray beam 306 through the phantom 302. Because the phantom 302 has a circular cross-section, the pathlength $L_2$ may be predictably calculated based on the geometry of a circle. Further, the pathlength $L_2$ is smaller than the pathlength $L_1$ due to the pathlength $L_1$ being equal to the diameter of the phantom 302. An example of calculating the pathlength for the vertical displacement X will be described below with respect to the method of FIG. 6. Further, as will be elaborated with respect to FIG. 6, since x-ray attenuation depends on the product of density and pathlength, the change in pathlength simulates different densities at a same pathlength, which enables contrast between the first imaging configuration 300 and the second imaging configuration 320 to be calculated. It may be understood that when the cross-section has a different shape, the pathlengths may be calculated based on geometric relationships of the corresponding shape.

Note that while FIG. 3 includes a vertical adjustment between the first imaging configuration 300 and the second imaging configuration 320, in other examples, the position of the phantom 302 may be adjusted along another direction. For example, although the x-ray source 304 and the detector array 308 are aligned such that the x-ray beam 306 is horizontal and parallel to the y-axis of the reference axes 399 in the example shown in FIG. 3, the x-ray source 304 and the detector array 308 may be rotated with respect to the central axis 390 in other embodiments. As an illustrative example, the x-ray source 304 and the detector array 308 may instead be aligned such that x-ray beam 306 is vertical and parallel to the x-axis of reference axes 399, such as when the phantom 302 is suspended over the edge of the table 312. In such an example, a horizontal adjustment (e.g., translation) may be used, wherein the phantom 302 is adjusted from a first y-direction position in the first imaging configuration 300 to a second y-direction position in the second imaging configuration 320 to result in a horizontal displacement Y. The horizontal displacement Y may be used to calculate the pathlength change through the phantom 302 in a similar manner to the vertical displacement X. Further, some systems may enable movement of the table 312 in a plurality of directions, and the x-ray source 304 and the detector array 308 may be arbitrarily positioned with respect to the reference axes 399. Thus, the discussion of using a vertical adjustment to adjust the pathlength of the x-ray beam 306 through the phantom 302 is provided by way of example, and other analogous arrangements may be used to produce a known change in the pathlength through the phantom 302 without departing from the scope of this disclosure.

Turning now to FIG. 4, a single imaging configuration 400 that may be used to determine the CNR by imaging the phantom 302 is shown. The single imaging configuration 400 is the same as the first imaging configuration 300 of FIG. 3, as described above. An x-ray beam 406 that is emitted from the x-ray source 304 at a second angle 414 penetrates the phantom 302 with a pathlength $L_3$ and travels directly to a second detector pixel 410. The second angle 414 is different than the first angle 314, and the second detector pixel 410 is at a different (e.g., lower) vertical position than the first detector pixel 310. The pathlength $L_3$ may be calculated based on the position of the second detector pixel 410 relative to the phantom 302 and the x-ray source 304, as will be elaborated below with respect to FIG. 7. It may be understood that the x-ray beam 306 and the x-ray beam 406 may be emitted simultaneously. Thus, the CNR may be evaluated based on measurements at the same detector pixel location (e.g., the first detector pixel 310) for different imaging configurations, as shown in FIG. 3, and/or based on measurements at different detector pixel locations for a same imaging configuration, as shown in FIG. 4.

FIG. 5 shows a first imaging configuration 500 and a second imaging configuration 520 that may be used to determine the CNR of the CT system. Unlike the configurations shown in FIGS. 3 and 4, the views shown in FIG. 5 are in the z-y plane. For example, each of the first imaging configuration 500 and the second imaging configuration 520 show table 312 from above (e.g., from the positive x-direction). Further, FIG. 5 shows a phantom 502 that is different than the phantom 302 of FIGS. 3 and 4. The phantom 502 has a non-uniform composition such that different slices along the z-direction may have a different material density or atomic number relative to each other. In the example shown in FIG. 5, the phantom 502 includes a first slice 504 of a first composition, a second slice 506 of a second composition, and a third slice 508 of a third composition. The first slice 504 may be comprised of water, for example, while the second slice 506 may be comprised of a mixture of water and iodine contrast which has a different atomic number compared to water. As another example, the third slice 508 may be comprised of polyethylene or polyvinylchloride. In other embodiments, one or more slices may comprise two or more forms (e.g., allotropes) of the same material having different densities, such as amorphous carbon as a first form and graphite as a second form. As such, different slices of the phantom 502 may include different material densities or atomic number relative to each other.

In the embodiment shown, the phantom 502 is cylindrical and includes the constant radius R along its length (e.g., in the z-direction). Further, the radius R may be the same or different than the phantom 302 of FIGS. 3 and 4. However, in other embodiments, the radius (or diameter) of the phantom 502 may vary along its length. For example, different slices of the phantom 502 may have different diameters with respect to each other. Further, while the phantom 502 includes a circular cross-section, other known geometries having a predictable variable width cross-section may be used, such as discussed above with respect to FIG. 3.

In the first imaging configuration 500, the phantom 502 is positioned such that the x-ray beam 306 penetrates the first slice 504 with a pathlength $L_4$ before reaching the first detector pixel 310. The pathlength $L_4$ may be the same as the pathlength $L_1$ of FIG. 3, such as when the phantom 302 has the same radius as the first slice 504. The table 312 is translated in the z-direction between the first imaging configuration 500 and the second imaging configuration 520, resulting in a horizontal displacement Z. The x-ray beam 306 penetrates the phantom 502 in the second slice 506 with the pathlength $L_4$ before reaching the first detector pixel 310 of the detector array 308. Thus, in the example shown, the pathlength does not change between the first imaging configuration 500 and the second imaging configuration 520, but the density of the imaged slice changes, thus enabling contrast between the two scans to be calculated.

The CNR provides a measurement of a fundamental capability of a CT system hardware in terms of dose efficiency. For example, an administrator of the CT system or a vendor may wish to evaluate new CT system hardware to determine whether purchasing the new CT system hardware is warranted in terms of increases in the CNR. For example, increasing the CNR may increase an image quality of diagnostic images acquired with the CT system by making it easier to visualize details for structures of interest relative to background tissue.

Therefore, FIG. 6 shows a flow chart illustrating a method 600 for determining a CNR of a CT system by scanning a phantom having a variable width cross-section. The method 600 is described with respect to the system and components described above with respect to FIGS. 1-2 but may be carried out with other systems/components without departing from the scope of this disclosure. The method 600 and the rest of the methods included herein may be carried out according to instructions stored in non-transitory memory of a computing device (e.g., computing device 216 of FIG. 2).

Some embodiments of the present disclosure include acquisition of reference measurements. At 602, the method 600 optionally includes acquiring reference measurements of the CT system. Acquiring the reference measurements of the CT system may include acquiring a first scan without the phantom or any other imaging object positioned within a gantry of the CT system (e.g., the gantry 102 of FIG. 1). During the first scan, the x-ray source may be activated (e.g., via the x-ray controller 210 of FIG. 2) to emit radiation of a same dose that will be used while scanning the phantom. Alternatively, a different dose may be used if the change in detector signal that will occur with the change in dose can be estimated. A detector array of the CT system may measure the x-ray radiation that is emitted by the x-ray source. Because the x-ray radiation does not pass through an imaged object, the x-ray radiation is not attenuated by the imaged object. The reference measurements may give the unattenuated x-ray signal at the given radiation dose at a given detector pixel location, for example. In some embodiments, the x-ray source and the detector array of the CT system may be held stationary while acquiring the reference measurements. The first scan may include a plurality of views (e.g., 4000 independent view measurements), for example. Further, when multiple imaging configurations are to be used in determining the CNR, the same reference measurements may be used for more than one configuration, or reference measurements may be obtained in each imaging configuration.

At 604, the method 600 includes positioning the phantom in the CT system in a first imaging configuration. The phantom may be placed on an imaging table (e.g., the table 312 of FIGS. 3-5). Alternatively, the phantom may be held by a phantom holder at the end of the table. The table may be adjusted to position the phantom in the first imaging configuration via a table motor controller (e.g., the table motor controller 226 of FIG. 2). The first imaging configuration may include a first vertical position (e.g., table height) with respect to a central axis of the CT system and a first translation (e.g., a patient axis position, corresponding to a z-direction position of the reference axes 399 of FIGS. 3-5). The first imaging configuration may be a pre-determined position that places the phantom in a first known geometric relation with respect to the x-ray source and the detector array. In one example, the first imaging configuration aligns the phantom between the centermost channel of the detector array with the x-ray source such that a pathlength through the phantom between the x-ray source and a centermost detector pixel location is maximal (e.g., equal to a diameter of the phantom), such as described above with respect to FIG. 3.

At 606, the method 600 includes acquiring a first set of measurements of the phantom in the first imaging configuration. Acquiring the first set of measurements of the phantom in the first imaging configuration may include acquiring a plurality of views of the phantom in the first imaging configuration while holding the x-ray source and the detector array of the CT system stationary. For example, a static scan may be acquired, in which the x-ray source and the detector array are not rotated about the gantry, so that the geometry between the x-ray source, the phantom, and the detector array at each detector pixel location is unchanging in each of the plurality of views. The number of measurements in the first set of measurements may be equal to the plurality of views of the reference measurements, at least in some embodiments. While acquiring the first set of measurements, the x-ray source may be activated (e.g., via the x-ray controller 210 of FIG. 2) to emit x-ray radiation toward the phantom, and at least a portion of the x-ray radiation may pass through the phantom before being detected via the detector array. Each detector element of the detector array may output signals corresponding to intensities of the x-ray radiation at each detector pixel location of the detector array, such as described above with respect to FIG. 1. Notably, attenuation of the x-ray radiation by the phantom may increase as a pathlength of a particular x-ray beam through the phantom increases, which may decrease the intensity (or photon count) of the x-ray radiation measured at the corresponding detector pixel location.

At 608, the method 600 includes determining if a second imaging configuration is to be used. The second imaging configuration may comprise a second vertical position and/or a second translation of the phantom within the gantry. As such, the geometric relation of the phantom with respect to the x-ray source and the detector array is different in the second imaging configuration than the first imaging configuration. For example, the second imaging configuration may be a pre-determined position that places the phantom in a second known geometric relation with respect to the x-ray source and the detector array. As one example, the second imaging configuration may be used when the phantom is a non-uniform phantom wherein different slices (e.g., with respect to a central axis of the phantom) have a different material composition. As another example, the second imaging configuration may be used to change the pathlength through the phantom between the x-ray source and a particular detector pixel location. An advantage of the approaches in both of these examples is that the two measurements that will be compared are made by the same detector channel (e.g., detector pixel location). On the other hand, in still another example, the second imaging configuration may not be used when it is desirable to not adjust the geometric relation of the phantom with respect to the x-ray source and the detector array. In such approaches, the two measurements that will be compared are made by different detector channels. Reference measurements as described above may be helpful in such approaches.

If the second imaging configuration is not to be used, the method 600 proceeds to 610 and includes determining the CNR of the CT system based on measurements from different detector locations, such as will be described below with respect to FIG. 7. It may be understood that the method of FIG. 7 may be used in combination with the method 600. For example, the CNR of the CT system may be determined both using the second imaging configuration and based on measurements from the different detector locations in one or both of the first detector location and the second detector location. The method 600 may then end.

If the second imaging configuration is to be used, the method 600 proceeds to 612 and includes positioning the phantom in the CT system in the second imaging configuration. Positioning the phantom in the CT system in the second imaging configuration may include one or both of adjusting the table height of the imaging table, as optionally indicated at 614, and adjusting the translation of the imaging table, as optionally indicated at 616. The table height may be adjusted (e.g., via the table motor controller) to adjust the phantom to the second vertical position, which may be a pre-determined vertical position that results in a predictable vertical displacement of the phantom within the gantry between the first imaging configuration and the second configuration, such as described above with respect to FIG. 3. The table height may be adjusted in order to adjust (e.g., decrease) the pathlength through the phantom between the x-ray source and a given detector pixel location, such as mentioned above. Similarly, the table translation may be adjusted (e.g., via the table motor controller) to adjust the phantom to the second translation, which may be a pre-determined z-direction position with respect to the gantry in order to change the slice of the phantom that is positioned between the x-ray source and the x-ray detector, such as described above with respect to FIG. 5, resulting in a different material and/or pathlength of the phantom being imaged in the second imaging configuration compared with the first imaging configuration. As still another example, the table translation may be adjusted in y-direction in order to change the pathlength of the phantom being imaged without changing the imaged slice, such as discussed above with respect to FIG. 3.

At 618, the method 600 includes acquiring a second set of measurements of the phantom in the second imaging configuration. Acquiring the second set of measurements of the phantom in the second imaging configuration may include acquiring a plurality of views of the phantom in the second imaging configuration while holding the x-ray source and the detector array of the CT system stationary. The number of measurements in the second set of measurements may be equal to the first set of measurements of the phantom in the first imaging configuration, at least in some embodiments. The second set of measurements may be acquired similarly to the first set of measurements and the reference measurements, such as by using the same radiation dose and other x-ray source and detector array imaging settings. Notably, due to the change in the vertical position and/or translation of the phantom within the gantry, the attenuation of the x-ray radiation by the phantom and detected by a given detector pixel location may be different in the second imaging configuration than in the first imaging configuration (e.g., due to changes in the material of the imaged slice and/or pathlength).

For example, referring briefly to FIG. 8, histogram distributions 800 for a first set of measurements 802 of a phantom positioned in a first imaging configuration, represented by filled bars, and a second set of measurements 804 from the phantom positioned in a second imaging configuration, represented by unfilled bars, are shown. The vertical axis represents the number of measurements that resulted in a particular detector reading, and the horizontal axis represents the detector reading for a selected detector pixel location. In the present example, the first imaging configuration produces a longer pathlength through the phantom between an x-ray source and the selected detector pixel location than the second imaging configuration.

As can be seen in FIG. 8, the second set of measurements 804 is shifted with respect to the first set of measurements 802 due to the change in the pathlength between the first imaging configuration and the second imaging configuration. That is, the second set of measurements 804 is shifted toward higher detector readings than the first set of measurements 802 due to the decreased x-ray attenuation through the shorter pathlength of the second imaging configuration. This shift represents the contrast between the first set of measurements 802 and the second set of measurements 804, while the width of each histogram distribution represents the noise in the corresponding set of measurements.

Returning to FIG. 6, at 620, the method 600 includes determining pathlengths through the phantom for the first imaging configuration and the second imaging configuration. In some embodiments, the pathlengths may be determined at a single selected detector pixel location, whereas in other embodiments, the pathlengths may be determined for a plurality of selected detector pixel locations, such as will be described below with respect to FIG. 7. When a single detector pixel location is used, a first pathlength through the phantom between the x-ray source and a selected detector pixel location in the first imaging configuration may be defined as $L_1$. In examples where the phantom is centered in the first imaging configuration and has a circular cross-section, $L_1$ is equal to the known diameter of the phantom or twice the radius, R (e.g., $L_1=2R$). A second pathlength through the phantom between the x-ray source and the selected detector pixel location in the second imaging configuration may be defined as $L_2$. In examples where the pathlength changes due to the vertical adjustment of the imaging table and the phantom has a circular cross-section, the second pathlength may be calculated as $L_2=\sqrt{2R^2-X^2}$, wherein X is vertical displacement of the phantom between the first imaging configuration and the second imaging configuration (e.g., see FIG. 3). In other embodiments where the cross-section has a different variable-width geometry, the pathlengths may be calculated using known geometric relationships. In some embodiments, a pathlength difference may be determined by subtracting $L_2$ from $L_1$.

At 622, the method 600 includes determining a contrast and noise for the selected detector pixel location for each imaging configuration based on the pathlengths, the first set of measurements, and the second set of measurements. For example, a first density contrast may be determined for the first imaging configuration by multiplying an attenuation coefficient by the first pathlength, and a second density contrast may be determined for the second imaging configuration by multiplying the attenuation coefficient by the second pathlength. As another example, a density contrast difference may be determined based on a difference between a first average signal output at the selected detector pixel location for the first set of measurements and a second average signal output at the selected detector pixel location for the second set of measurements and the pathlength difference (e.g., an average signal difference between the first set of measurements and the second set of measurements at the selected detector pixel location). As another example, a first average phantom measurement and first standard deviation may be determined for the selected detector pixel location from the first set of measurements, and a second average phantom measurement and a second standard deviation may be determined for the selected detector pixel location from the second set of measurements. For example, the standard deviation of each set of measurements may represent the noise in the given set of measurements.

For example, the CNR may be determined using the following equation:

$$CNR = \frac{<O(n)> - <B(n)>}{0.5*(std(O(n)) + std(B(n)))}$$

where $O(n)$ refers to a measurement from the phantom in the second set of measurements at the given detector pixel location and n is the measurement number, $B(n)$ refers to the measurement from the phantom in the first set of measurements at the given detector pixel location, $<O(n)>$ refers to the mean of the second set of measurements, $<B(n)>$ refers to the mean of the first set of measurements, $std(O(n))$ refers to the standard deviation of the second set of measurements, and $std(B(n))$ refers to the standard deviation of the first set of measurements.

When the detector array is a photon counting detector, there will be multiple energy bin measurements from each detector pixel location. To calculate the CNR, different weights may be applied to different energy bins, and the weighted energy bins may be summed together. The weights may be derived to achieve a maximum CNR for the imaging task at hand. For example, optimal weighting or equal weighting may be used. As an example, there may be m number of bins. The method 600 may include deriving m weights for the m bins so that the final CNR is maximized when the weighted sum of the m energy bins is output. That is, the measurement at each bin may be multiplied by a corresponding weight, and the products may be summed to output a single value for each measurement. The resulting single value for each measurement number (n) may be used as described above. The method 600 may then end.

Continuing to FIG. 7, a flow chart of an example method 700 is shown for determining the CNR of the CT system using a single imaging system configuration. As mentioned above, the method 700 may be performed in combination with and/or as a part of the method 600 of FIG. 6.

At 702, the method 700 includes determining a pathlength of x-ray penetration through the phantom based on a detector pixel location relative to the x-ray source for a plurality of detector pixel locations. For example, an incidence angle of a given x-ray beam may be determined based on a given detector pixel location relative to the x-ray source, and this incidence angle may be used to determine the pathlength of through the phantom based on a known diameter (or radius) of the phantom and its relative position within the gantry, such as the table height and table translation. For example, a first pathlength may be determined for a first detector pixel location of the plurality of detector pixel locations, and a second pathlength may be determined for a second detector pixel location of the plurality of detector pixel locations. In some embodiments, the plurality of detector pixel locations may include more than two detector pixel locations.

At 704, the method 700 includes determining a contrast and a noise at each of the plurality of detector pixel locations based on the determined pathlength, the first set of measurements, and the reference measurements. Determining the contrast and noise at a given detector pixel location of the plurality of detector pixel locations may be performed similar to that described above at 622 of FIG. 6. For example, a first average phantom measurement and first standard deviation may be determined for the first detector pixel location, and a second average phantom measurement and a second standard deviation may be determined for the second detector pixel location. In some embodiments, the reference measurements may be used to ensure that differences in the measurements at each detector pixel location are due to changes in the pathlength through the phantom and not due to variations between detector channels, for example.

At 706, the method 700 includes determining the CNR of the CT system based on density contrast differences for each of the plurality of detector pixel locations and the reference measurements (e.g., acquired at 602). A CNR may be determined based on signal output differences between two detector pixel locations of the plurality of detector pixel locations in a similar manner to that described above at 622 of FIG. 6. For example, the first detector pixel location may provide O(n) while the second detector pixel location may provide B(n). The method 700 may then end.

FIG. 9 shows an example graph 900 of scans of a phantom in two different imaging configurations of a CT system (e.g., the CT system 100 of FIG. 1). The graph 900 shows photon counts (vertical axis) relative to detector pixel location (horizontal axis) of a detector array (e.g., the detector array 108 of FIG. 1) for a first dataset 902 (dashed plot) and a second dataset 904 (solid plot). The first dataset 902 corresponds to an average of a plurality of acquisitions in a first imaging configuration, such as the first imaging configuration 300 of FIG. 3. The second dataset 904 corresponds to an average of a plurality of acquisitions in a second imaging configuration wherein a table supporting the phantom has been adjusted by a known amount relative to the first imaging configuration. For example, the second imaging configuration may be the second imaging configuration 320 of FIG. 3. Further, the phantom used to acquire the first dataset 902 and the second dataset 904 may have a uniform composition (e.g., the phantom 302 of FIG. 3) such that adjusting a vertical height of the phantom by raising or lowering the table (e.g., the table 312 of FIG. 3) results in a pathlength difference through the phantom at each detector pixel location without changing the composition.

Photon count differences between the first dataset 902 and the second dataset 904 at one or more or the detector pixel locations may be determined and used to calculate the contrast. For example, a detector pixel location k1 measures counts c1 for the first dataset 902, where the phantom is in the first imaging configuration, and counts c2 for the second dataset 904, where the phantom is in the second imaging configuration. The counts c1 is greater than the counts c2. For example, a pathlength through the phantom between an x-ray source (e.g., the x-ray source 304 of FIG. 3) and the detector pixel location k1 may increase in the second imaging configuration relative to the first imaging configuration due to the adjustment of the vertical height of the phantom within the CT system. The difference between the pathlength through the phantom between the first imaging configuration and the second imaging configuration along with the difference between the counts c1 and the counts c2 may be used to determine a first CNR of the CT system, such as described above with respect to FIG. 6.

As another example, a detector pixel location k2 measures counts c3 for the first dataset 902 and counts c4 for the second dataset 904. The counts c4 is greater than the counts c3. For example, a pathlength through the phantom between the x-ray source and the detector pixel location k2 may decrease in the second imaging configuration relative to the first imaging configuration, resulting in less attenuation of the x-rays measured at the detector pixel location k2. As with the detector pixel location k1, the difference between the pathlength through the phantom between the first imaging configuration and the second imaging configuration along with the difference between the counts c3 and the counts c4 may be used to determine a second CNR of the CT system. In embodiments where the detector array is a photon counting detector that collects data in multiple energy bins for each dataset, the data in each energy bin may be weighted and summed together before the CNR is determined, such as described above with respect to FIG. 6.

In some embodiments, a CNR of a CT system may be tracked over time, used to evaluate new hardware or hardware changes (e.g., the addition of a collimator), or as part of a diagnostic process to identify or rule out areas of CT system degradation. As such, FIG. 10 shows a flow chart of a method 1000 for evaluating changes in the CNR of the CT system in order to diagnose degradation in the CT system functionality. The method 1000 will be described with particular respect to the systems and components shown in FIGS. 1 and 2, although it may be understood that other systems may be used without departing from the scope of this disclosure.

At 1002, the method 1000 includes determining a first CNR at a first time point and/or first CT system hardware configuration. For example, the first CNR may be determined by acquiring a plurality of measurements from a phantom having a variable width cross-section (e.g., the phantom 302 of FIGS. 3 and 4 or the phantom 502 of FIG. 5) using the method of FIG. 6 and/or the method of FIG. 7. The first CNR may be timestamped (e.g., with a date and time that the first CNR is determined) and at least temporarily stored in memory. In some examples, additional metadata may be stored along with the first CNR, such as the particular phantom used in determining the CNR as well as imaging settings, such as the imaging configuration(s) used, a radiation dosage, and the like.

At 1004, the method 1000 includes determining a second CNR at a second time point and/or second CT system hardware configuration. When the same (first) CT system hardware configuration is assessed, the second time point may be one or more days or weeks after the first time point. Additionally or alternatively, the second time point may occur after imaging quality issues are detected with the CT system, such as will be elaborated below. When the second CT system hardware configuration is used, a duration between the first (e.g., earlier) time point and the second (e.g., later) time point may be shorter, such as a number of minutes or hours, at least in some embodiments. The second CT system hardware configuration may include adding, changing, or adjusting hardware of the CT system, such as adjusting a position of a post-patient collimator. In some embodiments, the second CNR may be determined based on measurements acquired while using the same phantom, imaging configuration(s), radiation dosage, and other settings used while acquiring measurements for determining the first CNR in order to provide a comparable value to the first CNR.

At 1006, the method 1000 includes determining a difference between the first CNR and the second CNR. For example, the second CNR may be compared to the first CNR so that deviations in the CNR of the CT system that occur over time or due to changes in the CT system hardware. The difference may be a magnitude difference (e.g., an absolute value of the difference) between the first CNR and the second CNR. In another example, the difference may be a percentage difference.

At 1008, the method 1000 includes determining if the difference is greater than a threshold (e.g., a greater than threshold change between the first CNR and the second CNR). The threshold may be a pre-determined, non-zero value or percentage, for example, that is stored in memory. When the difference is greater than the threshold, it may be determined that the CNR has gone out of an expected range, for example. In an alternative embodiment, instead of comparing the first CNR and the second CNR, the first CNR and the second CNR may be individually compared to the expected range, and it may be determined if one or both of the first CNR and the second CNR is outside of the expected range.

If the difference is greater than the threshold (or if the first CNR and/or the second CNR is outside of the expected range), the method 1000 proceeds to 1010 and includes indicating degradation in a detecting process of the CT system. Indicating the degradation in the detecting process of the CT system may include outputting a message or alert that specifies that the detecting process is degraded. For example, the message or alert may include an audio message, a chime or tone, and/or a visual, text-based message or symbol that indicates to an operator or administrator of the CT system that the detecting process of the CT system is degraded. As one example, the message or alert may be output via a display device, such as the display device 232 of FIG. 2. As another example, the message or alert may be additionally or alternatively output to a mobile device, such as a smartphone or tablet, associated with the operator or administrator of the CT system. In some embodiments, indicating the degradation in the detecting process of the CT system may optionally include indicating a suspected type of the degradation. For example, the message or alert may further indicate that the detecting process degradation is due to post-patient collimator misalignment, such as optionally indicated at 1012, or due to detector degradation, such as optionally indicated at 1014. For example, the post-patient collimator misalignment may be indicated when the position of the post-patient collimator has been adjusted between the first time point and the second time point. Further, the indication of the degradation in the detecting process of the CT system may advise the operator not to use the CT system to scan a patient until the source of the degradation is confirmed and remedied.

At 1020, the method 1000 includes performing an operation responsive to the indication of degradation. Performing the operation may include one or more of shutting down the CT system, disabling patient scans via the CT system, and recalibrating the CT system. For example, the method 1000 may output prompts to the operator or administrator of the CT system for performing the recalibration. The prompts may be output to the display device, for example, or via another device (e.g., via the mobile device). Further, the first CNR and the second CNR may be stored in memory so that the change in the CNR may be tracked over time. The method 1000 may then end.

Returning to 1008, if the difference is not greater than the threshold (e.g., the difference is less than or equal to the threshold, or both of the first CNR and the second CNR are within the expected range), the method 1000 proceeds to 1016 and includes determining if there is an image quality issue. For example, the operator may indicate that an image quality issue has developed between the first time point and the second time point via an operator console (e.g., operator console 220 of FIG. 2), or an algorithm (e.g., a deep learning algorithm) may identify poor image quality from acquisitions occurring after the first time point. The image quality issue may include poor contrast, high background noise, poor resolution, and/or another type of image quality issue that may degrade a diagnostic value of the acquired images.

If an image quality issue is present, the method 1000 proceeds to 1018 and includes indicating degradation of the x-ray source and/or an image processing algorithm used to generate the acquired images. For example, with the difference in the CNR not being greater than the threshold, changes in the image quality cannot be attributed to the detecting process, such as issues with the detector or other post-patient hardware (e.g., the post-patient collimator). Therefore, it may be assumed that the poor image quality is due to issues with the x-ray radiation being emitted toward the phantom (e.g., due to degradation of the x-ray source or other pre-patient hardware, such as a pre-patient collimator) or issues with how the computer is processing the signals received from the detector. The method 1000 may then proceed to 1020, such as described above.

If an image quality issue is not present, the method 1000 proceeds to 1022 and includes storing the first and second CNR values in memory to track the CNR of the CT system over time. As such, each subsequently determined CNR may be compared to a previously determined CNR in order to observe any deviations in the CNR over time that cannot be attributed to intentional changes in the CT system hardware configuration (e.g., installing a new detector, replacing the post-patient collimator, or the like). Further, the operator or administrator may retrieve the CNR values stored in memory to view a CNR history, for example. The method 1000 may then end. For example, the method 1000 may be repeated at a pre-determined frequency, such as daily, weekly, or monthly. As an example, a third CNR may be determined at a third time point following the second time point, and the third CNR may be compared to one or both of the first CNR and the second CNR (e.g., an average of the first CNR and the second CNR).

In this way, a CNR of a CT system may be evaluated using data collected by a detector array using a single phantom that is also used for quality control (e.g., a round water phantom) and without adding or removing phantom components from the CT system during the evaluation. In this way, the CNR may be more rapidly and easily obtained, enabling the CNR of both new and existing hardware to be quickly and accurately determined to aid in comparing an image quality of the new and existing hardware. Further, changes in the CNR may be identified over time, enabling a timely diagnosis of CT system degradation.

A technical effect of varying a position of a phantom having a variable width cross-section of a defined geometry within a CT system while acquiring measurements to determine a contrast-to-noise ratio of the CT system is that different pathlengths through the phantom may be achieved without adding or removing phantom components.

The disclosure also provides support for a method, comprising: positioning a phantom having a variable width cross-section within a gantry of a computed tomography (CT) system so that the variable width cross-section is perpendicular to a central axis of the CT system, adjusting the phantom within the gantry of the CT system to a first imaging configuration having a first position and a first translation within the gantry, acquiring a first set of measurements from the phantom in the first imaging configuration, and calculating a contrast-to-noise ratio (CNR) of the CT system based on at least the first set of measurements and a first material density of an imaged slice of the phantom in the first imaging configuration. In a first example of the method, acquiring the first set of measurements from the phantom in the first imaging configuration comprises collecting a plurality of views of the phantom in the first imaging configuration, each of the plurality of views comprising: emitting x-ray radiation from an x-ray source of the CT system toward the phantom, and outputting, via a detector array of the CT system, signals corresponding to intensities of the x-ray radiation at each of a plurality of detector pixel locations of the detector array. In a second example of the method, optionally including the first example, calculating the CNR of the CT system based on at least the first set of measurements comprises: determining a first pathlength of the x-ray radiation through the phantom at a first detector pixel location of the plurality of detector pixel locations, determining a second pathlength of the x-ray radiation through the phantom at a second detector pixel location of the plurality of detector pixel locations, determining a pathlength difference between the first pathlength and the second pathlength, determining an average signal output difference between a first average signal output at the first detector pixel location for the plurality of scans and a second average signal output at the second detector pixel location for the plurality of scans, and calculating the CNR of the CT system based on the pathlength difference and the average signal output difference. In a third example of the method, optionally including one or both of the first and second examples, performing the plurality of scans of the phantom in the first imaging configuration comprises holding the x-ray source and the detector array of the CT system stationary while acquiring the first set of measurements from the phantom. In a fourth example of the method, optionally including one or more or each of the first through third examples, the method further comprises: adjusting the phantom within the gantry of the CT system to a second imaging configuration having at least one of a different vertical position from the first position, different horizontal position from the first position, and a different translation from the first translation, acquiring a second set of measurements from the phantom in the second imaging configuration of the CT system, and calculating the CNR of the CT system further based on the second set of measurements. In a fifth example of the method, optionally including one or more or each of the first through fourth examples, adjusting the phantom within the gantry of the CT system to the second imaging configuration comprises adjusting a table position of an imaging table, wherein the imaged slice is constant between the first imaging configuration and the second imaging configuration, and wherein calculating the CNR of the CT system further based on the second set of measurements comprises: determining a first pathlength of the x-ray radiation through the phantom at a selected detector pixel location of the plurality of detector pixel locations, determining a second pathlength of the x-ray radiation through the phantom at the selected detector pixel location of the plurality of detector pixel locations, determining a pathlength difference between the first pathlength and the second pathlength, determining an average signal output difference between a first average signal output at the selected detector pixel location for the first set of measurements and a second average signal output at the selected detector pixel location for the second set of measurements, and calculating the CNR of the CT system based on the pathlength difference and the average signal output difference. In a sixth example of the method, optionally including one or more or each of the first through fifth examples, adjusting the phantom within the CT system to the second imaging configuration comprises adjusting a translation of an imaging table along the central axis of the CT system, and acquiring the second set of measurements from the phantom in the second imaging configuration comprises acquiring the second set of measurements from a second slice of the phantom comprising a second material density that is different than the first material density, and wherein calculating the CNR of the CT system is further based on the second material density. In a seventh example of the method, optionally including one or more or each of the first through sixth examples, the method further comprises: tracking the CNR of the CT system over time, and indicating degradation of the CT system in response to greater than a threshold change in the CNR over time. In an eighth example of the method, optionally including one or more or each of the first through seventh examples, calculating the CNR of the CT system based on at least the first set of measurements and the first material density of the imaged slice of the phantom in the first imaging configuration is performed without positioning an additional phantom component within the CT system. In a ninth example of the method, optionally including one or more or each of the first through eighth examples, the variable width cross-section is a circular cross-section that has a constant diameter along a length of the phantom, and wherein the length of the phantom is parallel to the central axis of the CT system.

The disclosure also provides support for a method, comprising: acquiring a plurality of measurements of a phantom having a variable width cross-section via an imaging system comprising an x-ray source and an x-ray detector, including acquiring a first portion of the plurality of measurements using a first pathlength of x-ray radiation through the phantom and a second portion of the plurality of measurements using a second pathlength of x-ray radiation through the phantom, and determining a contrast-to-noise ratio (CNR) of the imaging system based on a signal difference at the x-ray detector between the first portion of the plurality of measurements and the second portion of the plurality of measurements and a pathlength difference between the first pathlength and the second pathlength. In a first example of the method, acquiring the plurality of measurements occurs at a first time point, the CNR is a first CNR, and the method further comprises: acquiring a second plurality of measurements of the phantom via the imaging system at a second time point, including acquiring a first portion of the second plurality of measurements using the first pathlength of x-ray radiation through the phantom and a second portion of the second plurality of measurements using the second pathlength of x-ray radiation through the phantom, determining a second CNR of the imaging system based on a second signal difference at the x-ray detector between the first portion of the second plurality of measurements and the second portion of the second plurality of measurements and the pathlength difference between the first pathlength and the second pathlength, and comparing the first CNR to the second CNR to identify degradation of the imaging system. In a second example of the method, optionally including the first example, comparing the first CNR to the second CNR to identify the degradation of the imaging system comprises: indicating degradation of a detecting process of the imaging system in response to a difference between the first CNR and the second CNR being greater than a threshold, indicating degradation of at least one of the x-ray source and an image processing algorithm in response to the difference between the first CNR and the second CNR being less than or equal to the threshold while an image quality issue is indicated, and storing each of the first CNR and the second CNR in memory in response to the difference between the first CNR and the second CNR being less than or equal to the threshold while the image quality issue is not indicated. In a third example of the method, optionally including one or both of the first and second examples, indicating degradation of the detecting process of the imaging system comprises indicating degradation of one of the x-ray detector and a pre-detector collimator positioned between the phantom and the x-ray detector. In a fourth example of the method, optionally including one or more or each of the first through third examples: the first portion of the plurality of measurements and the second portion of the plurality of measurements are acquired at a same detector pixel location of the x-ray detector, the first portion of the plurality of measurements is acquired while the phantom is in a first position with respect to the x-ray source and the x-ray detector, the second portion of the plurality of measurements is acquired while the phantom is in a second position with respect to the x-ray source and the x-ray detector, and the pathlength difference is determined based on a displacement between the first position and the second position and a geometry of the phantom. In a fifth example of the method, optionally including one or more or each of the first through fourth examples: the first portion of the plurality of measurements is acquired a first detector pixel location of the x-ray detector, the second portion of the plurality of measurements is acquired at a second detector pixel location of the x-ray detector, different than the first detector pixel location, the first portion of the plurality of measurements and the second portion of the plurality of measurements are acquired while the phantom is in a same position with respect to the x-ray source and the x-ray detector, and the pathlength difference is determined based on a first position of the first detector pixel location relative to the x-ray source and the phantom, a second position of the second detector pixel location relative to the x-ray source and the phantom, and a geometry of the phantom.

The disclosure also provides support for a system, comprising: an x-ray source configured to emit x-ray radiation toward a phantom to be imaged, the phantom having a variable width cross-section and positioned on an imaging table such that a length of the phantom is parallel to a table length of the imaging table, a detector that receives the x-ray radiation attenuated by the phantom, a computer configured with instructions in non-transitory memory that, when executed, cause the computer to: acquire a first plurality of measurements of the x-ray radiation transmitted through a first pathlength of the phantom, acquire a second plurality of measurements of the x-ray radiation transmitted through a second pathlength of the phantom, and calculate a contrast-to-noise ratio (CNR) of the system based on a signal difference between the first plurality of measurements and the second plurality of measurements and a pathlength difference between the first pathlength and the second pathlength. In a first example of the system, to acquire the first plurality of measurements of the x-ray radiation transmitted through the first pathlength of the phantom, the computer is configured with further instructions in the non-transitory memory that, when executed, cause the computer to: adjust the imaging table to a first imaging configuration that produces the first pathlength through the phantom between the x-ray source and a first detector pixel location, and acquire the first plurality of measurements at the first detector pixel location. In a second example of the system, optionally including the first example, to acquire the second plurality of measurements of the x-ray radiation transmitted through the second pathlength of the phantom, the computer is configured with further instructions in the non-transitory memory that, when executed, cause the computer to: adjust the imaging table to a second imaging configuration that produces the second pathlength through the phantom between the x-ray source and the first detector pixel location, and acquire the second plurality of measurements at the first detector pixel location. In a third example of the system, optionally including one or both of the first and second examples, to acquire the second plurality of measurements of the x-ray radiation transmitted through the second pathlength of the phantom, the computer is configured with further instructions in the non-transitory memory that, when executed, cause the computer to: acquire the second plurality of measurements at a second detector pixel location, different than the first detector pixel location, while acquiring the first plurality of measurements at the first detector pixel location, wherein the first imaging configuration produces the second pathlength through the phantom between the x-ray source and the second detector pixel location.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A method, comprising:
positioning a phantom having a variable width cross-section within a gantry of a computed tomography (CT) system so that the variable width cross-section is perpendicular to a central axis of the CT system;
adjusting the phantom within the gantry of the CT system to a first imaging configuration having a first position and a first translation within the gantry, where x-ray radiation emitted by the CT system has a first pathlength through the phantom;
acquiring a first set of measurements from the phantom in the first imaging configuration by collecting a plurality of views of the phantom in the first imaging configuration, where collecting each of the plurality of views comprises:
emitting x-ray radiation from an x-ray source of the CT system toward the phantom; and
outputting, via a detector array of the CT system, signals corresponding to intensities of the x-ray radiation at each of a plurality of detector pixel locations of the detector array; and
calculating a contrast-to-noise ratio (CNR) of the CT system based on at least the first set of measurements, a first material density, and the first pathlength of an imaged slice of the phantom in the first imaging configuration by:
determining the first pathlength of the x-ray radiation through the phantom at a first detector pixel location of the plurality of detector pixel locations;
determining a second pathlength of the x-ray radiation through the phantom at a second detector pixel location of the plurality of detector pixel locations;
determining a first pathlength difference between the first pathlength and the second pathlength;
determining a first average signal output difference between a first average signal output at the first detector pixel location for the plurality of views and a second average signal output at the second detector pixel location for the plurality of views; and
calculating the CNR of the CT system based on the first pathlength difference and the first average signal output difference.

2. The method of claim 1, wherein collecting the plurality of views of the phantom in the first imaging configuration comprises holding the x-ray source and the detector array of the CT system stationary while acquiring the first set of measurements from the phantom.

3. The method of claim 1, further comprising:
adjusting the phantom within the gantry of the CT system to a second imaging configuration having at least one of a different vertical position from the first position, a different horizontal position from the first position, and a different translation from the first translation;
acquiring a second set of measurements from the phantom in the second imaging configuration of the CT system; and
calculating the CNR of the CT system further based on the second set of measurements.

4. The method of claim 3, wherein adjusting the phantom within the gantry of the CT system to the second imaging configuration comprises adjusting a table position of an imaging table, wherein the imaged slice is constant between the first imaging configuration and the second imaging configuration, and wherein calculating the CNR of the CT system further based on the second set of measurements comprises:
determining a third pathlength of the x-ray radiation through the phantom at a selected detector pixel location of the plurality of detector pixel locations;
determining a fourth pathlength of the x-ray radiation through the phantom at the selected detector pixel location of the plurality of detector pixel locations;
determining a second pathlength difference between the third pathlength and the fourth pathlength;
determining a third average signal output difference between a third average signal output at the selected detector pixel location for the second set of measurements and a fourth average signal output at the selected detector pixel location for the second set of measurements; and
calculating the CNR of the CT system based on the second pathlength difference and the third average signal output difference.

5. The method of claim 3, wherein adjusting the phantom within the CT system to the second imaging configuration comprises adjusting a translation of an imaging table along the central axis of the CT system, and acquiring the second set of measurements from the phantom in the second imaging configuration comprises acquiring the second set of measurements from a second slice of the phantom comprising a second material density that is different than the first material density, and wherein calculating the CNR of the CT system is further based on the second material density.

6. The method of claim 1, further comprising:
tracking the CNR of the CT system over time, the CNR calculated based on the first pathlength; and
indicating degradation of the CT system in response to greater than a threshold change in the CNR over time.

7. The method of claim 1, wherein calculating the CNR of the CT system based on at least the first set of measurements and the first material density of the imaged slice of the phantom in the first imaging configuration is performed without positioning an additional phantom component within the CT system.

8. The method of claim 1, wherein the variable width cross-section is a circular cross-section that has a constant diameter along a length of the phantom, and wherein the length of the phantom is parallel to the central axis of the CT system.

9. A method, comprising:
acquiring a plurality of measurements of a phantom having a variable width cross-section via an imaging system comprising an x-ray source and an x-ray detector, including acquiring a first portion of the plurality of measurements using a first pathlength of x-ray radiation through the phantom and a second portion of the plurality of measurements using a second pathlength of x-ray radiation through the phantom; and
determining a contrast-to-noise ratio (CNR) of the imaging system based on a signal difference at the x-ray detector between the first portion of the plurality of measurements and the second portion of the plurality of measurements and a pathlength difference between the first pathlength and the second pathlength.

10. The method of claim 9, wherein acquiring the plurality of measurements occurs at a first time point, the CNR is a first CNR, and the method further comprises:
acquiring a second plurality of measurements of the phantom via the imaging system at a second time point, including acquiring a third portion of the second plurality of measurements using the first pathlength of x-ray radiation through the phantom and a fourth portion of the second plurality of measurements using the second pathlength of x-ray radiation through the phantom;

determining a second CNR of the imaging system based on a second signal difference at the x-ray detector between the third portion of the second plurality of measurements and the fourth portion of the second plurality of measurements and the pathlength difference between the first pathlength and the second pathlength; and comparing the first CNR to the second CNR to identify degradation of the imaging system.

11. The method of claim 10, wherein comparing the first CNR to the second CNR to identify the degradation of the imaging system comprises:

indicating degradation of a detecting process of the imaging system in response to a difference between the first CNR and the second CNR being greater than a threshold;

indicating degradation of at least one of the x-ray source and an image processing algorithm in response to the difference between the first CNR and the second CNR being less than or equal to the threshold while an image quality issue is indicated; and storing each of the first CNR and the second CNR in memory in response to the difference between the first CNR and the second CNR being less than or equal to the threshold while the image quality issue is not indicated.

12. The method of claim 11, wherein indicating degradation of the detecting process of the imaging system comprises indicating degradation of one of the x-ray detector and a pre-detector collimator positioned between the phantom and the x-ray detector.

13. The method of claim 9, wherein:

the first portion of the plurality of measurements and the second portion of the plurality of measurements are acquired at a same detector pixel location of the x-ray detector;

the first portion of the plurality of measurements is acquired while the phantom is in a first position with respect to the x-ray source and the x-ray detector;

the second portion of the plurality of measurements is acquired while the phantom is in a second position with respect to the x-ray source and the x-ray detector; and the pathlength difference is determined based on a displacement between the first position and the second position and a geometry of the phantom.

14. The method of claim 9, wherein:

the first portion of the plurality of measurements is acquired a first detector pixel location of the x-ray detector;

the second portion of the plurality of measurements is acquired at a second detector pixel location of the x-ray detector, different than the first detector pixel location;

the first portion of the plurality of measurements and the second portion of the plurality of measurements are acquired while the phantom is in a same position with respect to the x-ray source and the x-ray detector; and the pathlength difference is determined based on a first position of the first detector pixel location relative to the x-ray source and the phantom, a second position of the second detector pixel location relative to the x-ray source and the phantom, and a geometry of the phantom.

15. A system, comprising:

an x-ray source configured to emit x-ray radiation toward a phantom to be imaged, the phantom having a variable width cross-section and positioned on an imaging table such that a length of the phantom is parallel to a table length of the imaging table;

a detector that receives the x-ray radiation attenuated by the phantom;

a computer configured with instructions in non-transitory memory that, when executed, cause the computer to:

acquire a first plurality of measurements of the x-ray radiation transmitted through a first pathlength of the phantom;

acquire a second plurality of measurements of the x-ray radiation transmitted through a second pathlength of the phantom; and calculate a contrast-to-noise ratio (CNR) of the system based on a signal difference between the first plurality of measurements and the second plurality of measurements and a pathlength difference between the first pathlength and the second pathlength.

16. The system of claim 15, wherein to acquire the first plurality of measurements of the x-ray radiation transmitted through the first pathlength of the phantom, the computer is configured with further instructions in the non-transitory memory that, when executed, cause the computer to:

adjust the imaging table to a first imaging configuration that produces the first pathlength through the phantom between the x-ray source and a first detector pixel location; and acquire the first plurality of measurements at the first detector pixel location.

17. The system of claim 16, wherein to acquire the second plurality of measurements of the x-ray radiation transmitted through the second pathlength of the phantom, the computer is configured with further instructions in the non-transitory memory that, when executed, cause the computer to:

adjust the imaging table to a second imaging configuration that produces the second pathlength through the phantom between the x-ray source and the first detector pixel location; and acquire the second plurality of measurements at the first detector pixel location.

18. The system of claim 16, wherein to acquire the second plurality of measurements of the x-ray radiation transmitted through the second pathlength of the phantom, the computer is configured with further instructions in the non-transitory memory that, when executed, cause the computer to:

acquire the second plurality of measurements at a second detector pixel location, different than the first detector pixel location, while acquiring the first plurality of measurements at the first detector pixel location, wherein the first imaging configuration produces the second pathlength through the phantom between the x-ray source and the second detector pixel location.

* * * * *